US011548919B1

United States Patent
Nahhas et al.

(10) Patent No.: US 11,548,919 B1
(45) Date of Patent: Jan. 10, 2023

(54) SARS-COV-2 POLYPEPTIDE INHIBITORS DIRECTED AGAINST THE ENV TM DOMAIN AND METHODS OF TREATMENT USING SAID INHIBITORS

(71) Applicant: King Abdulaziz University, Jeddah (SA)

(72) Inventors: Alaa F. Nahhas, Jeddah (SA); Thomas Webster, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/696,104

(22) Filed: Mar. 16, 2022

(51) Int. Cl.
*C07K 14/005* (2006.01)
*A61P 31/14* (2006.01)

(52) U.S. Cl.
CPC ............ *C07K 14/005* (2013.01); *A61P 31/14* (2018.01); *C07K 2319/00* (2013.01); *C12N 2770/20022* (2013.01); *C12N 2770/20032* (2013.01); *C12N 2770/20034* (2013.01)

(58) Field of Classification Search
CPC ........... C12N 2770/20022; C12N 2770/20032; C12N 2770/20034
See application file for complete search history.

(56) References Cited

PUBLICATIONS

Li, F., Feb. 2015, Receptor recognition mechanisms of coronaviruses: a decade of structural studies, J. Virol. 89(4):1954-1964.*
Abdelrahman, Z., et al., Sep. 2020, Comparative review of SARS-CoV-2, SARS-CoV, MERS-CoV, and inluenaz A respiratory viruses, Frontiers Immunol. 11:552909, pp. 1-14.*
Wang, M.-Y., et al., Nov. 2020, SARS-CoV-2: structure, biology, and structure-based therapeutics development, Frontiers Cell. Infect. Microbiol. 10:587269, pp. 1-17.*
Castillo-Diaz et al., "Self-Assembling Peptides as an Emerging Platform for the Treatment of Metabolic Syndrome", International Journal of Nanomedicine 2020:15, 10349-10370.
Chai et al., "Structural basis for SARS-CoV-2 envelope protein recognition of human cell junction protein PALS1", Nature Communications (2021) 12:3433.
Matsuzaki et al., "A comparative study on interactions of alpha-aminoisobutyric acid containing antibiotic peptides, trichopolyn I and hypelcin A with phosphatidylcholine bilayers", Biochim Biophys Acta. Dec. 9, 1991; 1070(2):419-28.
Panchal et al., "Peptide-Based Inhibitors for SARS-CoV-2 and SARS-CoV", Adv. Therap. 2021, 4, 2100104.
Schutz et al., "Peptide and peptide-based inhibitors of SARS-CoV-2 entry", Advanced Drug Delivery Reviews 167 (2020) 47-65.
Su et al., "Protein- and Peptide-Based Virus Inactivators: Inactivating Viruses Before Their Entry Into Cells", Frontiers in Microbiology, May 2020, vol. 11, Article 1063.

* cited by examiner

Primary Examiner — Jeffrey S Parkin
(74) Attorney, Agent, or Firm — WCF IP

(57) ABSTRACT

Methods for treating coronavirus infection, such as an infection caused by SARS-CoV-2, in a subject in need thereof include administering to the subject a therapeutically effective amount of a composition comprising an isolated polypeptide targeting the spike protein and the transmembrane region of the coronavirus envelope protein. Compositions include isolated polypeptides complementary to residues 30-38 of the envelope protein transmembrane region.

11 Claims, 7 Drawing Sheets

Specification includes a Sequence Listing.

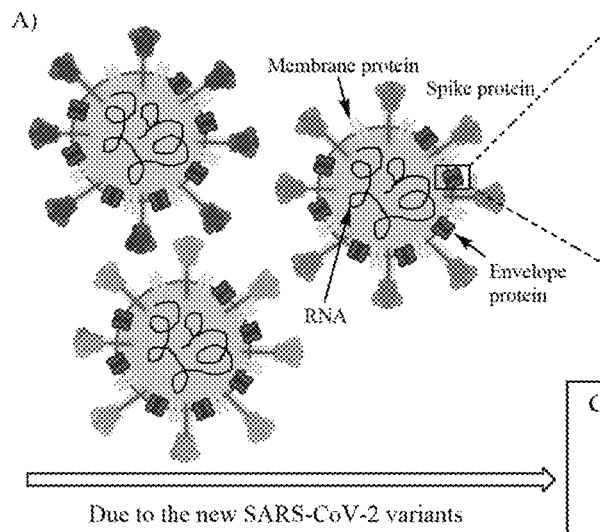
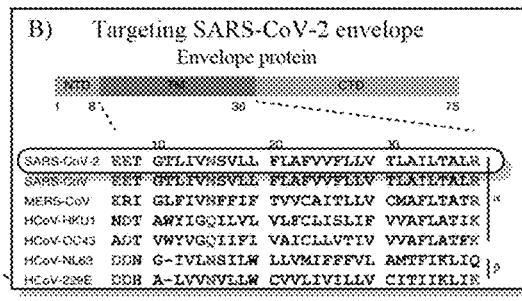
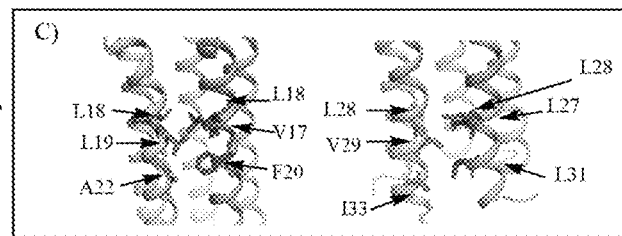
FIG. 1A
FIG. 1B
FIG. 1C

FIG. 3A
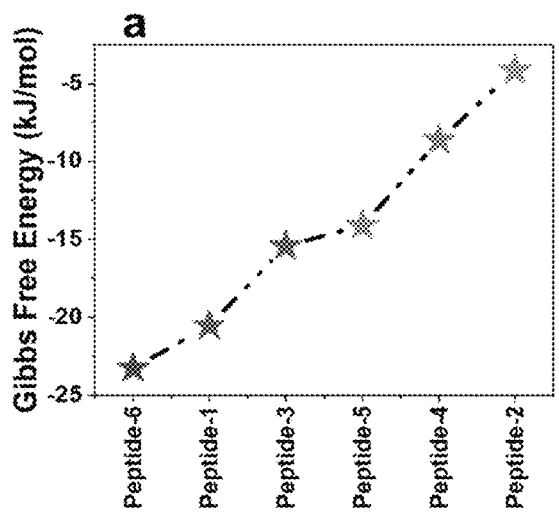
FIG. 3B
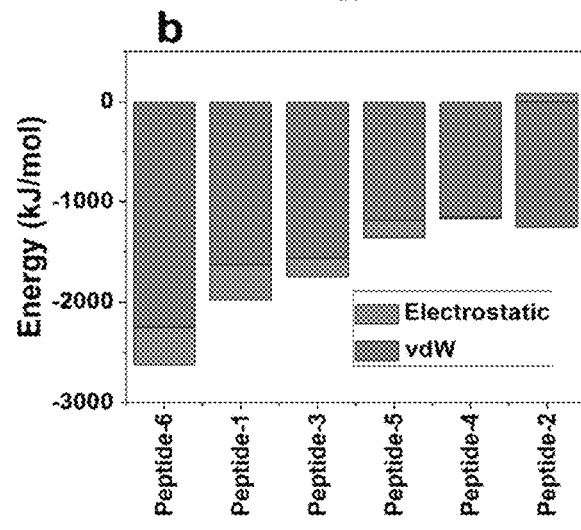
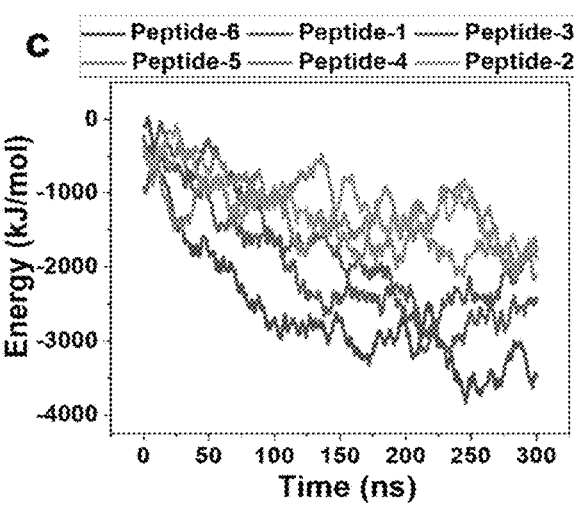
FIG. 3C

FIG. 4A
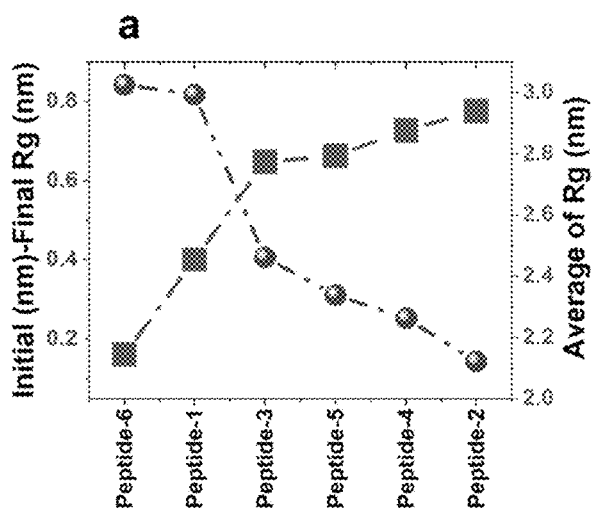
FIG. 4B
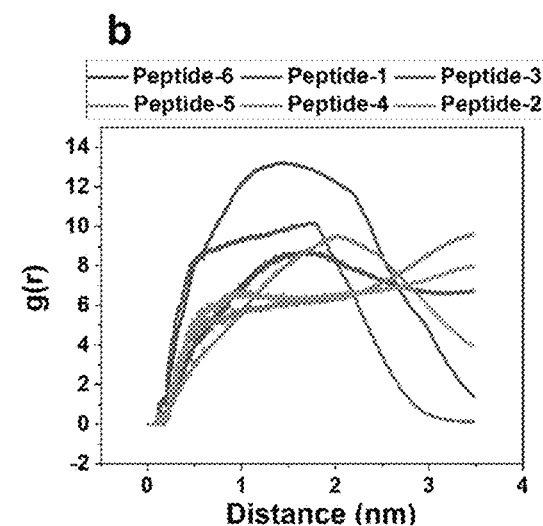
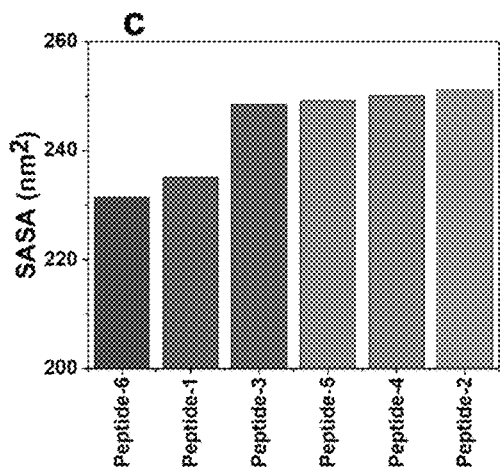
FIG. 4C

SARS-COV-2 POLYPEPTIDE INHIBITORS DIRECTED AGAINST THE ENV TM DOMAIN AND METHODS OF TREATMENT USING SAID INHIBITORS

SEQUENCE LISTING

This document incorporates by reference an electronic sequence listing text file, which was electronically submitted along with this document. The text file is named 15640127AAseqlisting_ST25, is 7 kilobytes, and was created on Mar. 9, 2022.

FIELD OF THE INVENTION

The invention is generally related to the use of polypeptides targeting spike and envelope proteins for treating a coronavirus infection, such as an infection caused by SARS-CoV-2.

BACKGROUND OF THE INVENTION

Severe acute respiratory syndrome coronavirus-2 (SARS-CoV-2) has created an unprecedented global health crisis. It is a zoonotic virus with highly contagious properties as compared to the Middle East Respiratory Syndrome virus (MERS-CoV). SARS-CoV-2 is from the Coronaviridae family and causes an acute respiratory disease which could be lethal, with about a 10.2% mortality rate. The disease can cause death due to severe alveolar destruction and hemorrhage as well as progressive respiratory failure.

According to the US Centers for Disease Control (CDC) website (1), numerous SARS-CoV-2 variants appeared during the winters of 2020-2022. Specifically, B.1.1.7 (20I/S01Y.V1) appeared in September 2020, B.1.351 (20H/S01Y.V2) in October 2020, P.1 (20J/S01Y.V3) in January 2021, B.1.617.2 (Delta Plus) and Omicron (B.1.1.529) in late 2021. It is believed that Omicron spread from Gauteng to the world faster than any prior SARS-CoV-2 variants (1). According to the University of Hong Kong, despite this faster rate of spread even in the presence of travel restrictions, the Omicron replication rate in the lung is 10 times lower than the Delta variant. It was also determined that the Omicron variant spread in countries with relatively high vaccination rates ranging from 69% and 77%, like Denmark and the UK (29, 30). Collectively, it is clear that there is an urgent need to find a new therapeutic solution for SARS-CoV-2 and all of its variants rather than the traditional approach of developing new boosters and asking the public to take new boosters for every new variant. This is especially true since the CDC shows that less people have taken a booster shot than the original vaccine. Specifically, greater than 211 million people are fully vaccinated in the US, however, only about 86 million have received the primary vaccine with a booster (31).

Many researchers are using small molecules which can only attach to the spike proteins and when doing so, such molecules do not inhibit other virus-mammalian cell attachment regions. A small peptide containing 8 residues was unable to block the whole SARS-CoV-2 surface area because it was too short to form a secondary structure (13). There are many studies which target the spike protein alone of the virus to inhibit virus interaction with the angiotensin-I-converting enzyme-2 (ACE2) of the host cell. For example, Han and Kral designed a peptide according to the ACE2 structure to inhibit the binding site between it and SARS-CoV-2 (14). However, new antiviral agents targeting coronaviruses are still needed.

SUMMARY

The present disclosure provides polypeptides targeting the coronavirus spike and envelope proteins that are useful for treatment of coronavirus infections. In particular, the polypeptides are complementary to the transmembrane region of the envelope protein.

An aspect of the disclosure provides an isolated polypeptide comprising the following amino acid consensus sequence: NapFF-$X_1$-L-$X_2$-F-L-$X_3$-$X_4$-$X_5$-E (SEQ ID NO: 16), wherein $X_1$, $X_3$, and $X_5$ are independently selected from T, S, and M; and $X_2$ and $X_4$ are independently selected from U and A. In some embodiments, the polypeptide is or includes one of SEQ ID Nos 1-6. In some embodiments, the isolated polypeptide further comprises four lysine residues at the polypeptide C-terminus.

Another aspect of the disclosure provides a pharmaceutical composition comprising an isolated polypeptide as described herein and a pharmaceutically acceptable carrier.

Another aspect of the disclosure provides a method of inhibiting replication of a coronavirus viral particle, comprising contacting the viral particle with a composition comprising an isolated polypeptide as described herein. In some embodiments, the coronavirus is SAR-CoV-2.

Another aspect of the disclosure provides a method of treating coronavirus infection in a subject in need thereof, comprising administering to the subject a therapeutically effective amount of a composition comprising an isolated polypeptide as described herein. In some embodiments, the coronavirus is SAR-CoV-2.

BRIEF DESCRIPTION OF THE DRAWINGS

FIGS. 1A-C. A) Structure of SARS-CoV-2 containing the mutant spike protein, membrane protein, genetic material, and envelope protein; B) Amino acid sequence of the envelope coronavirus (adapted from (26)): SARS-CoV-2 (SEQ ID NO: 7), SARS-CoV (SEQ ID NO: 8), MERS-CoV (SEQ ID NO: 9), HCoV-HKU1 (SEQ ID NO: 10), HCoV-OC43 (SEQ ID NO: 11), HCoV-NL63 (SEQ ID NO: 12), and HCoV-229E (SEQ ID NO: 13); and C) the hydrophobic residues of the core envelope (adapted from (26)).

FIGS. 3A-C. A) Gibbs free energy of the peptides of interest to the present study and their associated spike protein interactions. B) vdW and electrostatic energy of the peptides and spike protein interactions. C) Total energy of the peptide and spike protein interactions versus time.

FIGS. 4A-C. A) Differences between the initial and final gyration radius and average gyration radius of the peptide after interactions with the spike protein. B) Radial distribution function of the peptides after interactions with the spike protein. C) Solvent accessible surface area of the peptide after interactions with the spike protein.

DETAILED DESCRIPTION

Figure 2:
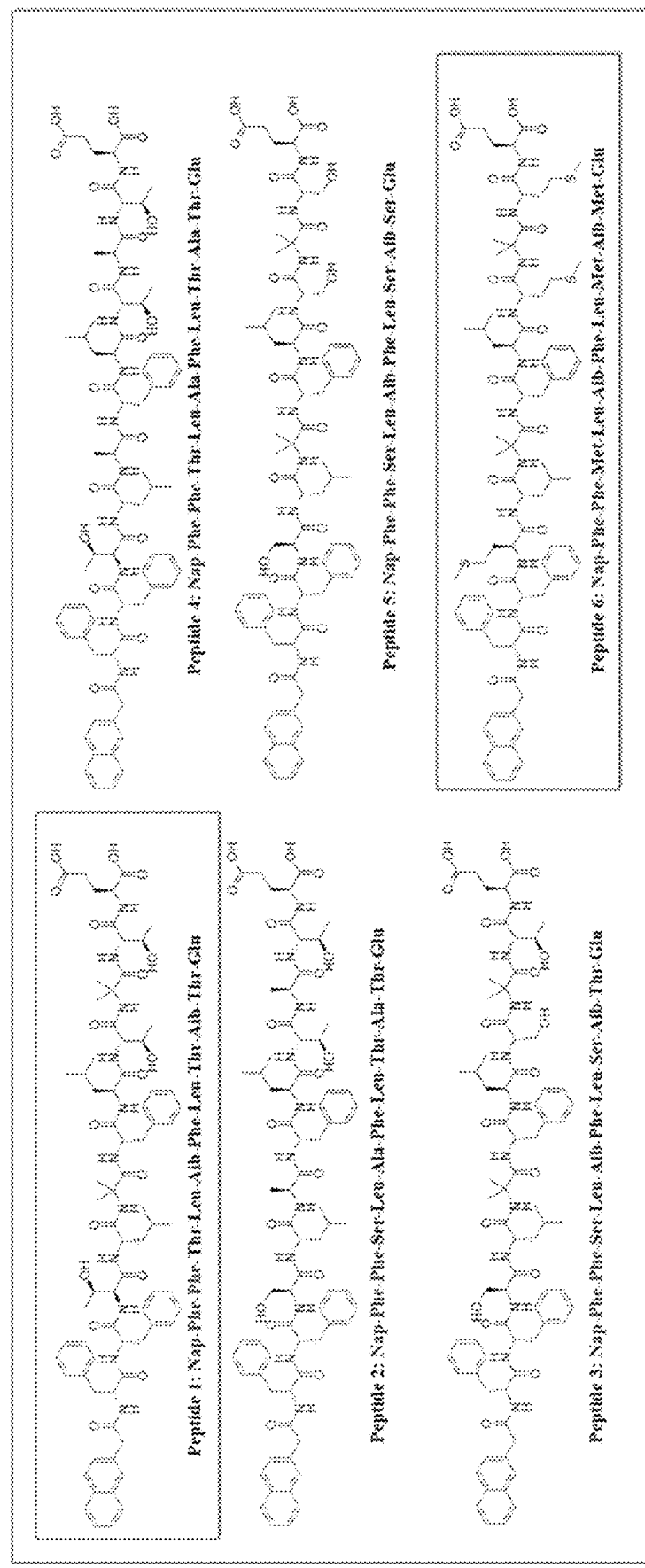
FIG. 2. The proposed six peptide sequences that are complementary to the transmembrane region (from 30-38) in the envelope protein of SARS-CoV-2. The peptides are Peptide 1: NapFFTLUFLTUTE (SEQ ID NO: 1), Peptide 2: NapFFSLAFLTATE (SEQ ID NO: 2), Peptide 3: NapFFSLUFLSUTE (SEQ ID NO: 3), Peptide 4: NapFFTLAFLTATE (SEQ ID NO: 4), Peptide 5: NapFFSLUFLSUSE (SEQ ID NO: 5), and Peptide 6: NapFFMLUFLMUME (SEQ ID NO: 6).

Embodiments of the disclosure provide isolated polypeptides that are useful for inhibiting replication of coronaviruses and variants thereof. The peptides can act as competitive inhibitors and can inhibit the virus from assembling. The peptides are less likely to be influenced by a coronavirus mutation, contain hydrophobic amino acids in the viral envelope for targeting, and are large enough to mask additional virus-mammalian cell attachment sites compared to traditional approaches.

By "isolated" or "purified" it is meant, when referring to a polypeptide sequence, that the indicated molecule is present in the substantial absence of other biological macromolecules of the same type. The term "purified" as used herein preferably means at least 75% by weight, more preferably at least 85% by weight, still preferably at least 95% by weight, and most preferably at least 98% by weight, of biological macromolecules of the same type are present.

Coronaviruses are a group of related RNA viruses that cause diseases in mammals and birds. In humans and birds, they cause respiratory tract infections that can range from mild to lethal. Mild illnesses in humans include some cases of the common cold (which is also caused by other viruses, predominantly rhinoviruses), while more lethal varieties can cause SARS, MERS, and COVID-19. Coronaviruses constitute the subfamily Orthocoronavirinae, in the family Coronaviridae, order Nidovirales, and realm Riboviria. The coronaviridae subfamily is further categorized into four genera: α-, β-, γ-, and δ-coronaviruses according to the classification of the Worldwide Committee for Logical Classification of Infections. They are enveloped viruses with a positive-sense single-stranded RNA genome and a nucleocapsid of helical symmetry. The genome size of coronaviruses ranges from approximately 26 to 32 kilobases. Exemplary coronaviruses that may be treated with the compositions of the disclosure include, but are not limited to, SARS-CoV, SARS-CoV-2, MERS-CoV, HCoV-OC43, HCoV-HKU1, HCoV-229E, and HCoV-NL63.

With reference to FIG. 1A, coronaviruses contain three mains parts: i) spike proteins (S) that bind to the host cell membrane surface helping the virus enter into mammalian cells, ii) membrane proteins that help in virus assembly, and iii) envelop proteins (E) that form cation selective channels across the endoplasmic reticulum—Golgi intermediate compartment on the host membrane to help in the pathogenicity of the virus. The envelope protein E has 75 residue viroporin molecules which are all viral hydrophobic proteins facilitating the virus release from infected cells. The amino acid sequence of this domain is shown in FIG. 1B.

According to the CDC, all of the SARS-CoV-2 variants that have appeared in the United Kingdom, South Africa, Brazil, and Japan have a conserved sequence in the transmembrane region of their envelop proteins, meaning that the mutation did not occur in this region as shown in Table 1.

TABLE 1

Characteristic mutations of multiple SARS-CoV-2 variants from September 2020-January 2021 according to the CDC.

| The countries in which the variant appeared first | Coronavirus variant | First identification date | Mutations in SARS-CoV-2 proteins |
| --- | --- | --- | --- |
| United Kingdom | B.1.1.7 (20I/S01Y.V1) | September 2020 | ORF1ab: T1001I, A1708D, I2230T, del3675-3677 SGF<br>ORF8: Q27 stop, R52I, Y73C<br>S: del69-70 HV, del144 Y, N501Y, A570D, D614G, P681H, T761I, S982A, D1118H<br>N: D3L, S235F |
| South Africa | B.1.351 (20H/S01Y.V2) | October 2020 | ORF1ab: K1655N<br>E: P71L<br>N: T205I<br>S: K417N, E484K, N501Y, D614G, A701V |
| Brazil and Japan | P. 1 (20J/S01Y.V3) | January 2021 | N: P80R<br>S: L18F, T20N, P26S, D138Y, R190S, K417T, E484K, N501Y, D614G, H655Y, T1027I<br>ORF1ab: F681L, I760T, S1188L, K1795Q, del3675-3677 SGF, E5662D<br>ORF3a: C174G<br>ORF8: E92K<br>ORF9: Q77E<br>ORF14: V49L |

TABLE 1-continued

Characteristic mutations of multiple SARS-CoV-2 variants from September 2020-January 2021 according to the CDC.

| The countries in which the variant appeared first | Coronavirus variant | First identification date | Mutations in SARS-CoV-2 proteins |
|---|---|---|---|
| India (State of Maharashtra) | B.1.617.2 (Delta Plus) | Late 2020 | Deletions at position H67, V70, and/or Y144<br>S: T19R, G142D, E156G,F157Δ,L452R, T478K, D614G, P681R, D90N<br>K417N mutation that is also found with Beta variant (27, 28) |

*ORF = Open reading frame; del = Deletion; S = Spike protein; N = Nucleocapsid protein; E = Envelope protein.

This conserved region is from amino acid number 8 to 38 (FIG. 1B). The polypeptides described herein are complementary to the transmembrane region of the envelope protein, e.g. to a region within residues 8-38, e.g. residues 30-38. The polypeptide may be 5-20 residues in length, e.g. about 8-12 residues, e.g. about 9 residues. The complementary sequences interact with each other through the self-assembly process or through non-coValent interactions.

In some embodiments, the polypeptides are capped at the N-terminus with a hydrogenator, NapFF (a naphthyl group followed by two phenylalanine residues), to enhance the self-assembly process.

In some embodiments, to increase the hydrophobicity of the peptide, α-aminoisobutyric acid (Aib, U) may be incorporated. Aib has the following structural formula $H_2N-C(CH_3)_2-COOH$. Aib may enhance the interaction between the peptide and cell membrane, increase the permeability into cells, and provide resistance to protease digestion. The Aib unnatural amino acid differs from the natural alanine amino acid in its extra methyl group at the α position of the C atom.

A polypeptide as described herein may comprise the following amino acid consensus sequence: NapFF-$X_1$-L-$X_2$-F-L-$X_3$-$X_4$-$X_5$-E (SEQ ID NO: 16), wherein $X_1$, $X_3$, and $X_5$ are independently selected from T, S, and M; and $X_2$ and $X_4$ are independently selected from U and A. In some embodiments, the polypeptide is or includes one of SEQ ID Nos 1-6 (FIG. 2).

The polypeptides described herein can be very hydrophobic in nature. To increase its polarity for use in a biological milieu, the isolated polypeptide may further comprise four lysine residues at its C-terminus.

The present disclosure further encompasses function-conservative variants of the polypeptides described herein. The function-conservative variants may result from modifications and changes that may be made in the structure of the polypeptides and in the DNA sequences encoding it, and still obtain a functional molecule with desirable characteristics (e.g. binding to coronavirus envelope protein).

Accordingly, "function-conservative variants" are those in which a given amino acid residue in a protein or enzyme has been changed without altering the overall conformation and function of the polypeptide, including, but not limited to, replacement of an amino acid with one having similar properties (such as, for example, polarity, hydrogen bonding potential, acidic, basic, hydrophobic, aromatic, and the like) Amino acids other than those indicated as conserved may differ in a protein so that the percent protein or amino acid sequence similarity between any two proteins of similar function may vary and may be, for example, from 70% to 99% as determined according to an alignment scheme such as by the Cluster Method, wherein similarity is based on the MEGALIGN algorithm. A "function-conservative variant" also includes a polypeptide which has at least 60% amino acid identity as determined by BLAST or FASTA algorithms, preferably at least 75%, more preferably at least 85%, still preferably at least 90%, and even more preferably at least 95%, and which has the same or substantially similar properties or functions as the native or parent protein to which it is compared. Two amino acid sequences are "substantially homologous" or "substantially similar" when greater than 80%, preferably greater than 85%, preferably greater than 90% of the amino acids are identical, or greater than about 90%, preferably greater than 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of sequence comparison algorithms such as BLAST, FASTA, etc.

For example, certain amino acids may be substituted for other amino acids in a protein structure without appreciable loss of antiviral activity. Since it is the interactive capacity and nature of a protein that defines that protein's biological functional activity, certain amino acid substitutions can be made in a protein sequence, and, of course, in its DNA encoding sequence, and nevertheless obtain a protein with like properties. It is thus contemplated that various changes may be made in the polypeptide sequences of the invention, or corresponding DNA sequences which encode said polypeptides, without appreciable loss of their biological activity.

Said binding and antiviral activity can be assessed by different techniques well-known in the art as described hereinafter.

In making the changes in the amino sequences of polypeptide, the hydropathic index of amino acids may be considered. The importance of the hydropathic amino acid index in conferring interactive biologic function on a protein is generally understood in the art. It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of their hydrophobicity and charge characteristics these are: isoleucine (+4.5); valine (+4.2); leucine (+3.8); phenylalanine (+2.8);

cysteine/cystine (+2.5); methionine (+1.9); alanine (+1.8); glycine (−0.4); threonine (−0.7); serine (−0.8); tryptophane (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

The polypeptides of the invention may be produced by any technique known per se in the art, such as, without limitation, any chemical, biological, genetic or enzymatic technique, either alone or in combination.

Knowing the amino acid sequence of the desired sequence, one skilled in the art can readily produce said polypeptides, by standard techniques for production of polypeptides. For instance, they can be synthesized using well-known solid phase method, preferably using a commercially available peptide synthesis apparatus (such as that made by Applied Biosystems, Foster City, Calif.) and following the manufacturer's instructions.

Alternatively, the polypeptides of the disclosure can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

Polypeptides of the disclosure can be use in an isolated (e.g., purified) form or contained in a vector, such as a membrane or lipid vesicle (e.g. a liposome).

In specific embodiments, it is contemplated that polypeptides according to the disclosure may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution.

Polypeptides and compositions containing the polypeptides as described herein may be used in vitro to inhibit replication of a coronavirus viral particle or used in vivo to treat a coronavirus infection. The in vitro method may include a step of contacting the viral particle with a composition comprising an isolated polypeptide as described herein under conditions sufficient to inhibit viral replication.

The term "treat/treating" refers to eliciting the desired biological response, i.e., a therapeutic effect which comprises one or more of a decrease/reduction in infection or infection symptom, a decrease/reduction in the severity of the infection (e.g., reduction or inhibition of viral adsorption, reduction or inhibition of viral replication, etc.), and an increased survival time of the affected host animal, following administration of the agent/composition.

Without being so limited, the medicaments/pharmaceutical compositions of the disclosure may be administered orally, for example in the form of tablets, coated tablets, dragees, hard or soft gelatin capsules, solutions, emulsions or suspensions. Administration can also be carried out rectally, for example using suppositories; locally, topically, or percutaneously, for example using ointments, creams, gels or solutions; or parenterally, e.g., intravenously, intramuscularly, subcutaneously, intrathecally or transdermally, using for example injectable solutions. Furthermore, administration can be carried out sublingually, nasally, or as ophthalmological preparations or an aerosol, for example in the form of a spray, such as a nasal spray.

The active agent (e.g. polypeptide) may be combined with pharmaceutically acceptable excipients/carriers. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. The medicaments/pharmaceutical compositions may also contain preserving agents, solubilizing agents, stabilizing agents, wetting agents, emulsifiers, sweeteners, colorants, odorants, salts for the variation of osmotic pressure, buffers, coating agents or antioxidants.

The compositions of the present disclosure may also contain other components such as, but not limited to, additives, adjuvants, buffers, tonicity agents, and preservatives. An additive such as a sugar, a glycerol, and other sugar alcohols, can be included in the compositions of the present disclosure. Pharmaceutical additives can be added to increase the efficacy or potency of other ingredients in the composition. For example, a pharmaceutical additive can be added to a composition of the present disclosure to improve the stability of the bioactive agent, to adjust the osmolality of the composition, to adjust the viscosity of the composition, or for another reason, such as effecting drug delivery. Non-limiting examples of pharmaceutical additives of the present disclosure include sugars, such as, saccharin trehalose, mannose, D-galactose, and lactose and flavorings such as orange oil.

In an embodiment, if a preservative is desired, the compositions may optionally be preserved with any well-known system such as benzyl alcohol with/without EDTA, benzalkonium chloride, chlorhexidine, Cosmocil® CQ, or Dowicil 200.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

The compositions can also be administered in combination therapy, e.g., combined with at least one other agent able to treat or inhibit coronavirus infection such as hexamethylene amiloride (HMA) or amantadine (AMT).

In some embodiments, the active agent (e.g. polypeptide) is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

SUMMARY

The present study focused on targeting the novel SARS-CoV-2 envelope protein which has not been frequently mutating and the S protein as well with a much larger peptide capable of inhibiting virus mammalian cell attraction. In doing so, molecular dynamics software was used here to model six peptides including: NapFFTLUFLTUTE (SEQ ID NO: 1), NapFFSLAFLTATE (SEQ ID NO: 2), NapFFSLUFLSUTE (SEQ ID NO: 3), NapFFTLAFLTATE (SEQ ID NO: 4), NapFFSLUFLSUSE (SEQ ID NO: 5), and NapFFMLUFLMUME (SEQ ID NO: 6). Results showed that two of these completely hydrophobic peptides (SEQ ID NO: 1 and SEQ ID NO: 6) had a strong ability to bind to the virus, preventing its binding to a mammalian cell membrane, entering the cell, and replicating by covering many attachment sites on the SARS-CoV-2.

Materials and Methods

Molecular dynamics (MD) simulation was used to study the interaction between peptides (from 1-6 as shown in FIG. 2) and the virus spike protein and their conformational changes over time (15-17). Parameters, such as Root Mean Square Deviation (RMSD), Root Mean Square Fluctuations (RMSF), and Radius of Gyration (Rg), were used in the simulation. RMSD measures the stability of peptide-virus interactions while RMSF is used to quantify the rigidity and flexibility between the peptide-virus complex. Rg is used to study the conformational changes and the folding properties in the complex. We modeled these peptides and tested their interaction with the spike protein of SARS-CoV-2 using Avogadro software (18). The molecular structure of the spike protein was obtained from the RCSB website using PDB ID 6M0J.

The stimulation of the spike protein was done using GROMACS 2019.5 software (19) in aqueous media in two independent coarse-grained simulations. Coarse-grained simulations are needed to determine interactions over a long period of time. Any changes between the spike proteins and the peptides were surveyed in 10 independent simulations. Also, all atomic simulations between the spike proteins and the peptides were studied using an OPLSA force field (17, 20, 21) and that was done by placing both in $10\times10\times10$ nm$^3$ boxes. The conditions used inside the box were 300 K and 1 bar using Parrinello_Rahman algorithms and v-rescale to equilibrate the system. The LINCS algorithm was used in the final stage of the stimulations with a cut-off radius of 1.5 nm with 2 fs and 100 ns for the H-bonds (22).

The same MD simulations between the spike protein and ACE2 receptor were used here by Shahbazi and their team (23) using autodock vina 112 Linux x86 software for the docking process (24). All of our simulations were done in triplicate.

Results

Evaluation of the Effect of the Peptide Nanomaterials on the SARS-CoV-2 Spike Protein We first examined the interaction between these six peptides and the deformation of the virus spike protein: Peptide 1: NapFFTLUFLTUTE (SEQ ID NO: 1), Peptide 2: NapFFSLAFLTATE (SEQ ID NO: 2), Peptide 3: NapFFSLUFLSUTE (SEQ ID NO: 3), Peptide 4: NapFFTLAFLTATE (SEQ ID NO: 4), Peptide 5: NapFFSLUFLSUSE (SEQ ID NO: 5), and Peptide 6: NapFFMLUFLMUME (SEQ ID NO: 6) (FIG. 3). The van der Waals (vdW) and electrostatic interactions were collectively considered as the total interaction energy between the peptides and the spike protein as shown in FIG. 3B. As shown in FIG. 3B, the vdW interaction was seen in all peptides showing a critical role in the total energy. Peptides 1 and 6 had the strongest binding with the spike protein (20-23 kJ/mole), respectively, as shown in FIG. 3A. These strong interactions between the peptides 1 or 6 with the spike protein led to the deformation of the spike protein. Also, a long time-scale simulation (300 ns) between all of these six peptides on the deformed spike protein was performed as shown in FIG. 3C to see the effect of these peptides on the deformation of the spike protein.

Evaluation of the Interaction of SARS-CoV-2 Spike Protein with the ACE2 Receptor One of the important ways to study the structural changes of the spike protein leading to the inhibition of binding to the host cell is to evaluate the binding affinity between the six peptides and the spike protein. During this interaction, the structure of the spike protein transformed from prefusion to post-fusion where it became similar to a long needle in shape [6,21]. According to these data, we examined the average radius of gyration and $\Delta Rg$ ($Rg_{final}-Rg_{initial}$) for these six hydrophobic peptides as shown in FIG. 4A. The spike protein distorted by peptides 1 and 6 as indicated with a high $\Delta Rg$ meant a higher Rg final value than $Rg_{initial}$ and the most extended structure, as shown in FIG. 4A. So, these results confirmed that peptides 1 and 6 exhibited an inhibitory effect on the virus.

The mean solvent accessible surface areas (SASA) of the spike protein and the six peptides are presented in FIG. 4C. By lowering the SASA value, as shown in peptides 1 and 6, the interaction with the spike protein was the strongest and the spike protein had the lowest contact area with the aqueous media, perhaps preventing it from spreading through the body. Collectively, this means that the deformation of the spike protein occurred. Such results indicated that these two hydrophobic peptides (1 and 6) compete with hydrophobic interactions between the virus spike protein and ACE2 as that suggested by Wang and his team (25).

Figure 5A:
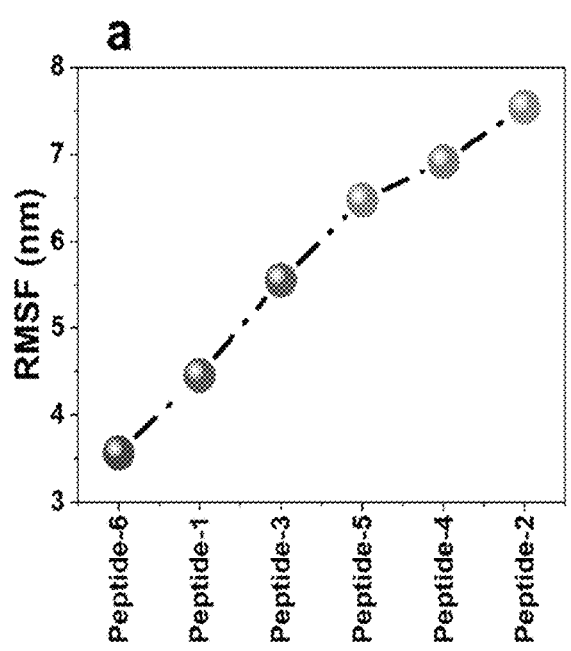
FIGS. 5A-B. A) Average RMSF of the peptide after interaction with the spike protein. B) Average RMSD of the peptide after interaction with the spike protein.
Figure 5B:
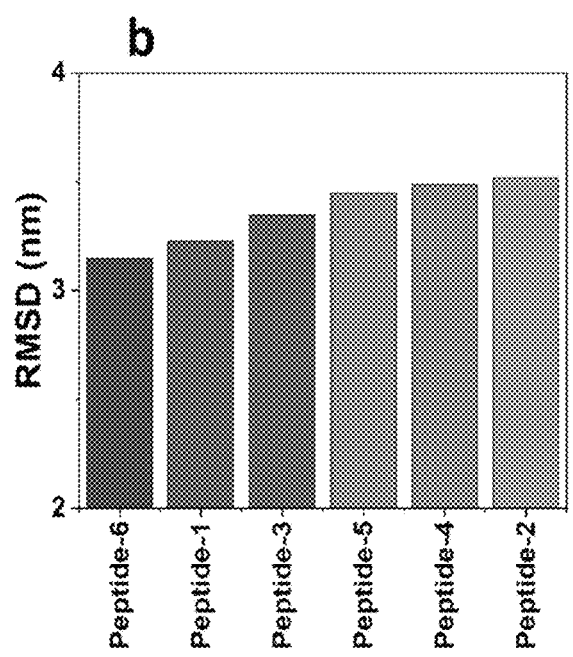

The average root-mean-square-distribution (RMSD) and the average root-mean-square-fluctuation (RMSF) were also used to study the stability of the peptide-spike protein complexes as shown in FIG. 5. The lower values in RMSF, as shown in FIG. 5A, indicated that the peptides 1 and 6 narrowed the broad range of fluctuations which was the same result obtained with RMSD as shown in FIG. 5B.

Conclusion

Despite the use of the Pfizer, Moderna, etc. vaccines and the appearance that the COVID-19 pandemic may thus be over, SARS-CoV-2 which causes COVID-19 is still mutating and fostering subsequent questions related to the efficacy of such vaccines. Here, in this study, we identified novel hydrophobic peptides designed to target the spike and envelope proteins and block many attachment sites on SARS-CoV-2. Results of this computational modeling study showed excellent interactions with the virus to inhibit virus replication. This study thus provides evidence for the use of these peptides for a wide range of COVID-19 complications, especially those associated with SARS-CoV-2 mutations, including for therapeutic and prophylactic treatments.

Acknowledgement

We would like to thank the Deanship of Scientific Research (DSR) at King Abdulaziz University, Jeddah, Saudi Arabia who funded this project, under grant no. KEP-15-130-42.

REFERENCES FOR EXAMPLE 1

1. Prevention CfDCa. Delta variant: What we know about the science 2021 [Available from: cdc.gov/coronavirus/2019-ncov/variants/delta-variant.html.
2. Weiss S R, Navas-Martin S. Coronavirus pathogenesis and the emerging pathogen severe acute respiratory syndrome coronavirus. Microbiol Mol Biol Rev. 2005; 69(4): 635-64.
3. Wilson L, McKinlay C, Gage P, Ewart G. SARS coronavirus E protein forms cation-selective ion channels. Virology. 2004; 330(1):322-31.
4. Verdia-Baguena C, Nieto-Torres J L, Alcaraz A, DeDiego M L, Torres J, Aguilella V M, et al. Coronavirus E protein forms ion channels with functionally and structurally-involved membrane lipids. Virology. 2012; 432(2):485-94.
5. Nieto-Torres J L, DeDiego M L, Verdia-Baguena C, Jimenez-Guardeño J M, Regla-Nava J A, Fernandez-Delgado R, et al. Severe acute respiratory syndrome coronavirus envelope protein ion channel activity promotes virus fitness and pathogenesis. PLoS pathogens. 2014; 10(5):e1004077.
6. Li Y, Surya W, Claudine S, Torres J. Structure of a conserved Golgi complex-targeting signal in coronavirus envelope proteins. The Journal of biological chemistry. 2014; 289(18):12535-49.
7. Torres J, Maheswari U, Parthasarathy K, Ng L, Liu D X, Gong X. Conductance and amantadine binding of a pore formed by a lysine-flanked transmembrane domain of SARS coronavirus envelope protein. Protein science: a publication of the Protein Society. 2007; 16(9):2065-71.
8. Zhang Y, Kuang Y, Gao Y, Xu B. Versatile Small-Molecule Motifs for Self-Assembly in Water and the Formation of Biofunctional Supramolecular Hydrogels. Langmuir. 2011; 27(2):529-37.
9. Nahhas A F, Chang R, Webster T J. Introducing unnatural amino acids-containing tripeptides as antimicrobial and anticancer agents. J Biomed Nanotechnol. 2018; 14(5): 987-93.
10. A FN, A FN, T JW. Nanoscale pathogens treated with nanomaterial-like peptides: a platform technology appropriate for future pandemics. Nanomedicine (Lond). 2021; 16(14):1237-54.
11. Badani H, Garry R F, Wimley W C. Peptide entry inhibitors of enveloped viruses: the importance of interfacial hydrophobicity. Biochimica et biophysica acta. 2014; 1838(9):2180-97.

12. Andrew Rambaut N L, Oliver Pybus, Wendy Barclay, Jeff Barrett, Alesandro Carabelli, Tom Connor, Tom Peacock, David L Robertson, Erik Volz, on behalf of COVID-19 Genomics Consortium UK (CoG-UK). Preliminary genomic characterisation of an emergent SARS-CoV-2 lineage in the UK defined by a novel set of spike mutations. nCoV-2019 Genomic Epidemiology. 2020.
13. Du Q, Wang S, Wei D, Sirois S, Chou K-C. Molecular modeling and chemical modification for finding peptide inhibitor against severe acute respiratory syndrome coronavirus main proteinase. Analytical biochemistry. 2005; 337(2):262-70.
14. Han Y, Kral P. Computational Design of ACE2-Based Peptide Inhibitors of SARS-CoV-2. ACS Nano. 2020; 14(4):5143-7.
15. Maleki R, Khedri M, Rezvantalab S, Afsharchi F, Musaie K, Shafiee S, et al. β-Amyloid Targeting with Two-Dimensional Covalent Organic Frameworks: Multi-Scale In-Silico Dissection of Nano-Biointerface. Chembiochem. 2021; 22(13):2306-18.
16. Alimohammadi E, Nikzad A, Khedri M, Rezaian M, Jahromi A M, Rezaei N, et al. Potential treatment of Parkinson's disease using new-generation carbon nanotubes: a biomolecular in silico study. Nanomedicine. 2021; 16(3):189-204.
17. Zandi P, Ghasemy E, Khedri M, Rashidi A, Maleki R, Miri Jahromi A. Shedding light on miniaturized dialysis using MXene 2D materials: A computational chemistry approach. ACS omega. 2021; 6(9):6312-25.
18. Hanwell M D, Curtis D E, Lonie D C, Vandermeersch T, Zurek E, Hutchison G R. Avogadro: an advanced semantic chemical editor, visualization, and analysis platform. Journal of Cheminformatics. 2012; 4(1):17.
19. Van Der Spoel D, Lindahl E, Hess B, Groenhof G, Mark A E, Berendsen H J C. GROMACS: Fast, flexible, and free. Journal of Computational Chemistry. 2005; 26(16): 1701-18.
20. Sohraby F, Soltanabad M H, Bagheri M, Javan M B, Moghadam M J, Baghkheirati E K, et al. Application of molecular dynamics in coating Ag-conjugated nanoparticles with potential therapeutic applications. Nano Biomed Eng. 2020; 12(1):90-8.
21. Li B, Hong S, Zhang X, Xiong C, Zhao G, Yang Q, et al. Understanding interfacial mechanics and mechanisms of exfoliation and stabilization of graphene using urea/glycerol solvents. Advanced Theory and Simulations. 2019; 2(12):1900155.
22. Alimohammadi E, Khedri M, Jahromi A M, Maleki R, Rezaian M. Graphene-based nanoparticles as potential treatment options for parkinson's disease: a molecular dynamics study. International Journal of Nanomedicine. 2020; 15:6887.
23. Khedri M, Maleki R, Dahri M, Sadeghi M M, Rezvantalab S, Santos H A, et al. Engineering of 2D nanomaterials to trap and kill SARS-CoV-2: a new insight from multi-microsecond atomistic simulations. Drug Delivery and Translational Research. 2021.
24. Arbeit J M, Toy B J, Karczmar G S, Hubesch A, Weiner M W. Inhibition of tumor high-energy phosphate metabolism by insulin combined with rhodamine 123. Surgery. 1988; 104(2):161-70.
25. Wang Y, Liu M, Gao J. Enhanced receptor binding of SARS-CoV-2 through networks of hydrogen-bonding and hydrophobic interactions. Proceedings of the National Academy of Sciences. 2020; 117(25):13967-74.
26. Mandala V S, McKay M J, Shcherbakov A A, Dregni A J, Kolocouris A, Hong M. Structure and Drug Binding of the SARS-CoV-2 Envelope Protein in Phospholipid Bilayers. Research square. 2020.
27. Arora P, Kempf A, Nehlmeier I, Graichen L, Sidarovich A, Winkler M S, et al. Delta variant (B.1.617.2) sublineages do not show increased neutralization resistance. Cellular & Molecular Immunology. 2021.
28. Mlcochova P, Kemp S A, Dhar M S, Papa G, Meng B, Ferreira I A T M, et al. SARS-CoV-2 B.1.617.2 Delta variant replication and immune evasion. Nature. 2021.
29. Pouwels K B, Pritchard E, Matthews P C, Stoesser N, Eyre D W, Vihta K-D, et al. Effect of Delta variant on viral burden and vaccine effectiveness against new SARS-CoV-2 infections in the UK. Nature Medicine. 2021; 27(12):2127-35.
30. Hansen C, Michlmayr D, Gubbels S, Mølbak K, Ethelberg S. Assessment of protection against reinfection with SARS-CoV-2 among 4 million PCR-tested individuals in Denmark in 2020: a population-level observational study. The Lancet. 2021; 397.
31. Prevention CfDCa. COVID data tracker weekly review 2022 [Available from: cdc.gov/coronavirus/2019-ncov/covid-data/covidview/index.html.
32. Nahhas A F, Chang R, Webster T J. Introducing Unnatural Amino Acids-Containing Tripeptides as Antimicrobial and Anticancer Agents. Journal of Biomedical Nanotechnology. 2018; 14(5):987-93.
33. Taniguchi K, Wada S-i, Ito Y, Hayashi J, Inomata Y, Lee S-W, et al. α-Aminoisobutyric Acid-Containing Amphipathic Helical Peptide-Cyclic RGD Conjugation as a Potential Drug Delivery System for MicroRNA Replacement Therapy in Vitro. Molecular Pharmaceutics. 2019; 16(11):4542-50.
34. Taylor J W, Kaiser E. [25] Structure-function analysis of proteins through the design, synthesis, and study of peptide models. Meth Enzymol. 1987; 154:473-98.
35. Voges K-P, Jung G, Sawyer W H. Depth-dependent fluorescent quenching of a tryptophan residue located at defined positions on a rigid 21-peptide helix in liposomes. Biochimica et Biophysica Acta (BBA)-Biomembranes. 1987; 896(1):64-76.
36. Lampel A, Elis E, Guterman T, Shapira S, Marco P, Bacharach E, et al. α-Aminoisobutyric acid incorporation induces cell permeability and antiviral activity of HIV-1 major homology region fragments. Chemical Communications. 2015; 51(62):12349-52.
37. Yamaguchi H, Kodama H, Osada S, Kato F, Jelokhani-Niaraki M, Kondo M. Effect of α, α-dialkyl amino acids on the protease resistance of peptides. Bioscience, biotechnology, and biochemistry. 2003; 67(10):2269-72.
38. Merrifield R B. Solid Phase Peptide Synthesis. I. The Synthesis of a Tetrapeptide.
Journal of the American Chemical Society. 1963; 85(14): 2149-54.
39. Xia S, Chan J F-W, Wang L, Jiao F, Chik K K-H, Chu H, et al. Peptide-based pan-CoV fusion inhibitors maintain high potency against SARS-CoV-2 Omicron variant. Cell Research. 2022.

Example 2

Summary

The SARS-CoV-2 Omicron variant is called a "variant of concern" (VOC) which has spread all over the world at a faster rate than even the first SARS-CoV-2 outbreak despite travel restrictions. In order to combat the health consequences from a SARS-CoV-2 Omicron variant infection, the objective of the present in vitro study was to develop self-assembled nano peptides to attach to the virus and inhibit its attachment and entry into mammalian cells for replication. For this purpose, two amphipathic peptides containing hydrophobic and hydrophilic peptides and an unnatural amino acid (such as 2-aminoisobutyric acid (U)) were designed to attach to the less mutated virus envelop region: NapFFTLUFLTUTEKKKK (SEQ ID NO: 14) and NapFFMLUFLMUMEKKKK (SEQ ID NO: 15). These peptides were synthesized using the solid phase peptide synthesis method and were characterized for mammalian cell infection using well-established pseudo virus assays. Results showed that the two self-assembled nano peptides significantly inhibited the ability of the SARS-CoV-2 Omicron variant virus to infect mammalian cells and replicate.

Materials and Methods

Peptide Synthesis

The peptides were synthesized manually under nitrogen bubbler gas using Fmoc solid peptide synthesis chemistry (38). Their structures were confirmed using proton nuclear magnetic resonance (H-NMR) and liquid chromatography-mass spectrometry (LC-MS) to confirm their molecular mass. The exact mass of NapFFTLUFLTUTEKKKK (SEQ ID NO: 14) is 1968.1125 and we obtained its fractions as 985.3, 657.4, and 493, and the exact mass of NapFFMLUFLMUMEKKKK (SEQ ID NO: 15) is 2058.0909 and we obtained its fraction as 1030.4, 687.4, and 515.9 m/z.

In Vitro Pseudovirus Experiment

The SARS-CoV-2 Omicron variant pseudo virus and mammalian cells were purchased from Creative Diagnostics (NY, USA) for this assay. The protocol used for this experiment can be found at: creative-diagnostics.com/news-human-ace2-stable-cell-line-hek293t-85.htm.

For the pseudovirus, we used the Lentiviral SARS-CoV-2 Omicron variant pseudovirus. To understand the mechanism of SARS-CoV-2 cell entry, it is essential to study how Spike proteins interact with the Angiotensin-Converting Enzyme 2 (ACE2) receptor. However, such studies are hampered by the danger of producing and manipulating live coronavirus. Live SARS-CoV-2 has to be handled under biosafety level 3 conditions, which has hindered the development of vaccines and therapeutics. Pseudo-viruses are useful virological tools because of their safety and versatility, as the pseudovirus is restricted to a single round of replication and can be handled using biosafety level 2 (BSL-2) containment practices.

The pseudotyped Luciferase/GFP rSARS-CoV-2 Spike displays antigenically correct spike protein pseudotyped upon replication but containing incompetent virus particles that contain a heterologous lentiviral (HIV) core and are capable of a single round of infection carrying a genome that expresses either a GFP or luciferase optical reporter gene upon infection. Pseudotyped Luciferase/GFP rSARS-CoV-2 Spikes are produced in HEK-293T cells using three separate plasmids, encoding the spike protein, a lentiviral gag polyprotein, and a reporter gene that can be used to test the ability of serum, antibodies, and drugs to neutralize the infectivity of the SARS-CoV-2 spike protein (FIG. 3).

HEK293T cells were used in this project. This cell line was constructed by the transduction of the human angiotensin I converting enzyme 2 (ACE2) into HEK293T cells, followed by stable cell selection. HEK293T is derived from HEK293 and is commonly used in scientific research. The HEK293T-human ACE2 cell line can be used for in vitro screening and characterization of drug candidates against SARS-CoV.

The peptides of interest in this study were added at various concentrations (from 0 to 0.001 mg/ml) to various concentrations of a SARS-CoV-2 Omicron pseudo virus (10 to $10^6$ copies/mi) added to a model mammalian cell (seeded at $10^4$ cells). Standard cell culture media (DMEM+10% FBS) was also added to the wells. The peptides were then allowed to interact with the pseudovirus and cells for 15 minutes under standard incubator conditions. After the prescribed time period, the samples were analyzed using a fluorimeter. All experiments were conducted in triplicate and repeated at three different time periods with appropriate controls, including no peptides, no cells, and no pseudovirus. Differences between fluorescence intensity was assessed using ANOVA and student t-tests with $p<0.01$ considered statistically significant.

Results and Discussion

The two synthetic amphipathic peptides NapFFTLUFLTUTEKKKK (SEQ ID NO: 14) and NapFFMLUFLMUMEKKKK (SEQ ID NO: 15) were synthesized and purified using preparative liquid chromatography and the structure of these two peptides were confirmed using LC-MS and H-NMR spectra.

Figure 6:
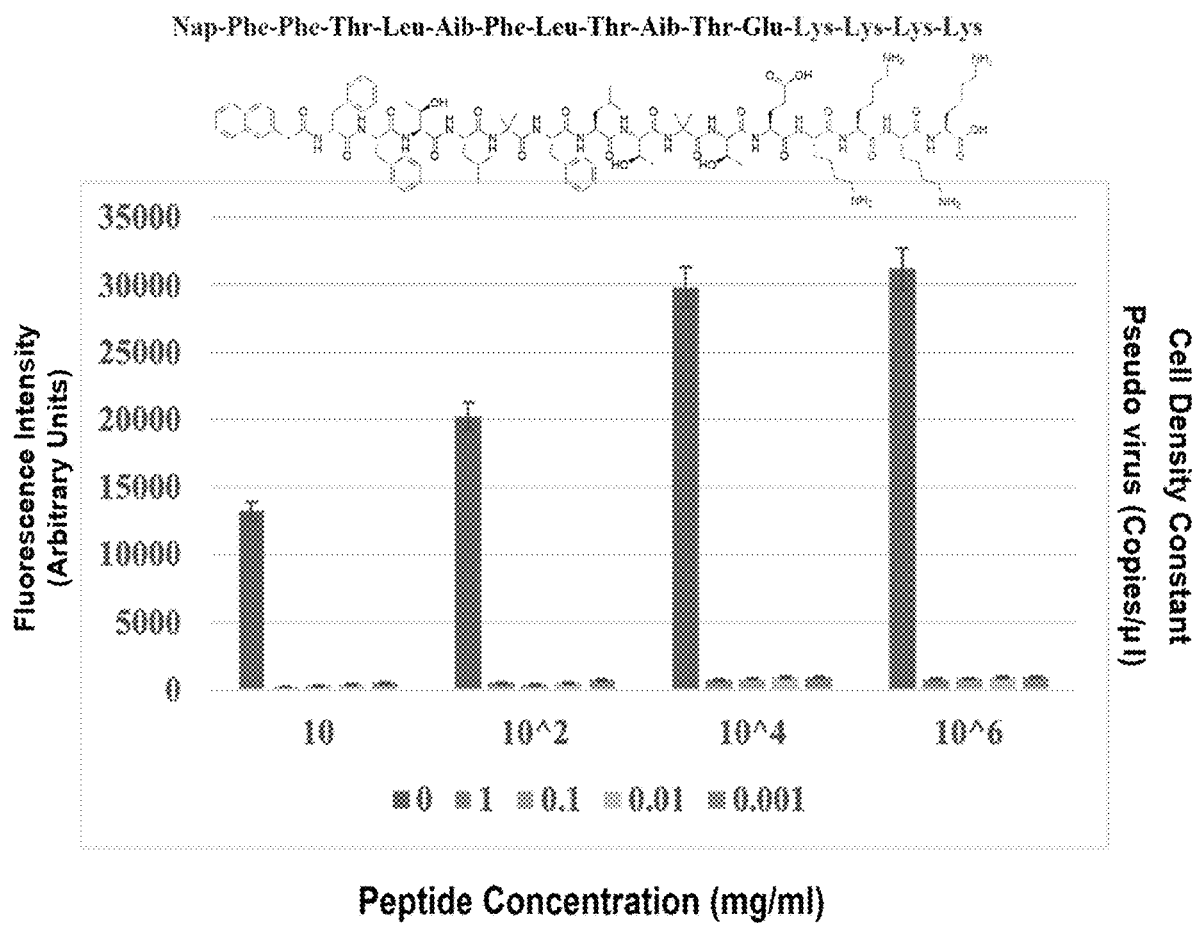
FIG. 6. The peptides were tested on human ACE2 stable cell line-HEK93. All controls, no cells and no pseudo virus showed no to minimal fluorescence within experimental error. All NapFFTLUFLTUTEKKKK (SEQ ID NO: 14) peptide groups were statistically (p<0.01) less than no NapFFTLUFLTUTEKKKK (SEQ ID NO: 14) (control). Time=15 minutes. Data=avg.+/−SEM; N=3.
Figure 7:
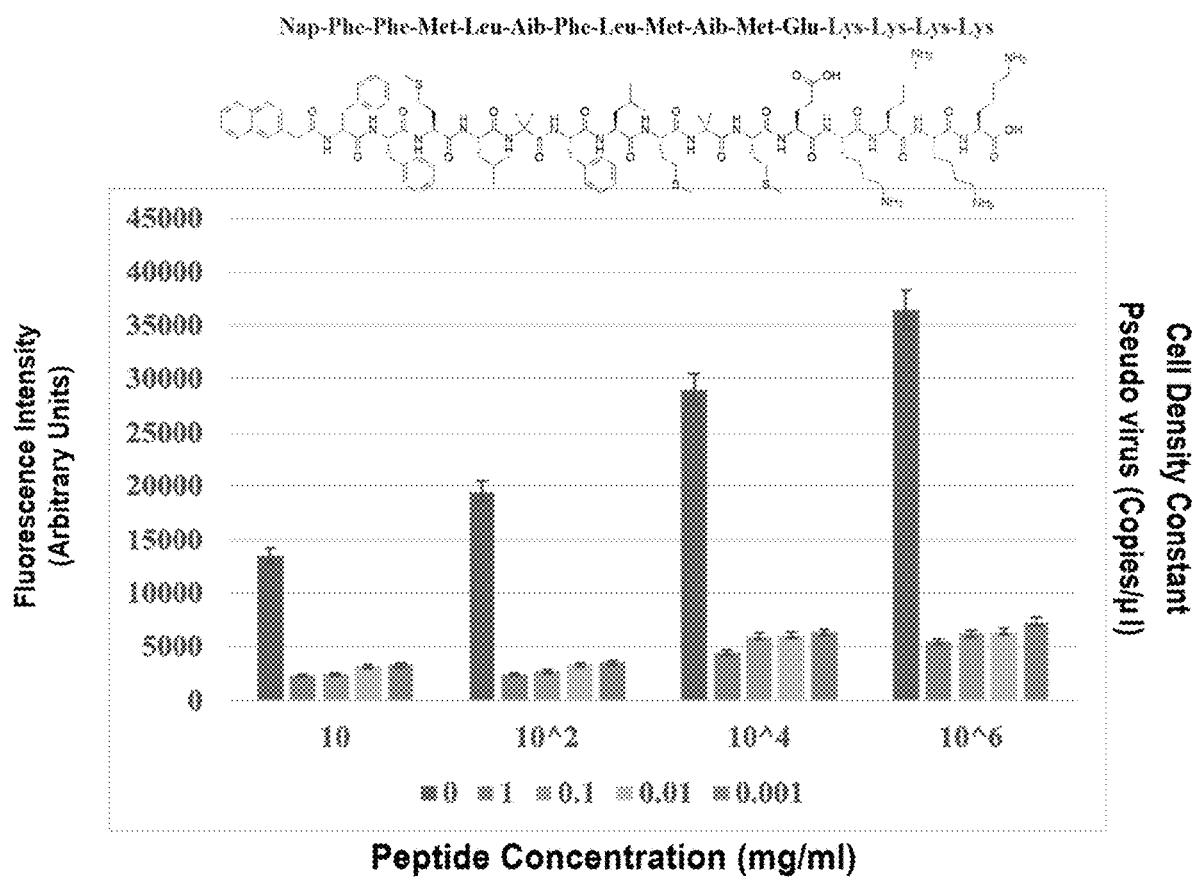
FIG. 7. The peptides were tested on human ACE2 stable cell line-HEK93. All controls, no cells and no pseudo virus showed no to minimal fluorescence within experimental error. All NapFFMLUFLMUMEKKKK (SEQ ID NO: 15) peptide groups were statistically (p<0.01) less than no NapFFMLUFLMUMEKKKK (SEQ ID NO: 15) (control). Time=15 minutes. Data=avg.+/−SEM; N=3.

There are peptides used by others to target the S-protein of SARS-CoV-2 such as EK1, EKL1C, and EK1C4 (39). However, we designed two peptides that target the viral envelope. The peptides were tested on an infected human ACE2 stable cell line-HEK93 and effectively inhibited Omicron pseudovirus (PsV) infection as shown in FIGS. 6 and 7. These are the first two peptides to our knowledge used to target the SARS-CoV-2 Omicron envelope.

Conclusion

In this study, we designed two amphipathic peptides NapFFTLUFLTUTEKKKK (SEQ ID NO: 14) and NapFFMLUFLMUMEKKKK (SEQ ID NO: 15) that contained the unnatural amino acid Aib to find a new nanomaterial to passivate the highly spreadable SARS-CoV-2 Omicron variant. The Aib unnatural amino acid differs from the natural Alanine amino acid in its extra methyl group at the a position of the C atom. We have shown that Aib increases the hydrophobicity of a compound and exhibits antibacterial and anticancer activity. These two peptides were synthesized using a well-known solid phase peptide synthesis strategy. In vitro SARS-CoV-2 Omicron pseudo virus studies showed that these two peptides effectively inhibited viral replication and, thus, are useful as a prophylactic or therapeutic for COVID-19.

ACKNOWLEDGMENT

We would like to thank the Deanship of Scientific Research (DSR) at King Abdulaziz University, Jeddah, Saudi Arabia who funded this project, under grant no. KEP-15-130-42.

REFERENCES

1 C. f. D. C. a. Prevention, (2021)
2 K. B. Pouwels, E. Pritchard, P. C. Matthews, N. Stoesser, D. W. Eyre, K.-D. Vihta, T. House, J. Hay, J. I. Bell, J. N. Newton, J. Farrar, D. Crook, D. Cook, E. Rourke, R. Studley, T. E. A. Peto, I. Diamond, and A. S. Walker, Nature Medicine. 27, 2127-2135 (2021)
3 C. Hansen, D. Michlmayr, S. Gubbels, K. Mølbak, and S. Ethelberg, The Lancet. 397, (2021)
4 C. f. D. C. a. Prevention, (2022)
5 Y. Zhang, Y. Kuang, Y. Gao, and B. Xu, Langmuir. 27, 529-537 (2011)

6 A. F. Nahhas, R. Chang, and T. J. Webster, J Biomed Nanotechnol. 14, 987-993 (2018)
7 F. N. A, F. N. A, and J. W. T, Nanomedicine (Lond). 16, 1237-1254 (2021)
8 A. F. Nahhas, R. Chang, and T. J. Webster, Journal of Biomedical Nanotechnology. 14, 987-993 (2018)
9 K. Taniguchi, S.-i. Wada, Y. Ito, J. Hayashi, Y. Inomata, S.-W. Lee, T. Tanaka, K. Komura, Y. Akao, H. Urata, and K. Uchiyama, Molecular Pharmaceutics. 16, 4542-4550 (2019)
10 J. W. Taylor, and E. Kaiser, Methods in enzymology. 154, 473-498 (1987)
11 K.-P. Voges, G. Jung, and W. H. Sawyer, Biochimica et Biophysica Acta (BBA)-Biomembranes. 896, 64-76 (1987)
12 A. Lampel, E. Elis, T. Guterman, S. Shapira, P. Marco, E. Bacharach, and E. Gazit, Chemical Communications. 51, 12349-12352 (2015)
13 H. Yamaguchi, H. Kodama, S. Osada, F. Kato, M. Jelokhani-Niaraki, and M. Kondo, Bioscience, biotechnology, and biochemistry. 67, 2269-2272 (2003)
14 R. B. Merrifield, Journal of the American Chemical Society. 85, 2149-2154 (1963)
15 S. Xia, J. F.-W. Chan, L. Wang, F. Jiao, K. K.-H. Chik, H. Chu, Q. Lan, W. Xu, Q. Wang, C. Wang, K.-Y. Yuen, L. Lu, and S. Jiang, Cell Research. (2022)

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. An isolated polypeptide comprising the following amino acid sequence:

NapFF-$X_1$-L-$X_2$-F-L-$X_3$-$X_4$-$X_5$-E wherein $X_1$, $X_3$, and $X_5$ are independently selected from T, S, and M; and $X_2$ and $X_4$ are independently selected from U and A.

2. The isolated polypeptide of claim 1, wherein the polypeptide is or includes SEQ ID NO:1.

3. The isolated polypeptide of claim 1, wherein the polypeptide is or includes SEQ ID NO:2.

4. The isolated polypeptide of claim 1, wherein the polypeptide is or includes SEQ ID NO:3.

5. The isolated polypeptide of claim 1, wherein the polypeptide is or includes SEQ ID NO:4.

6. The isolated polypeptide of claim 1, wherein the polypeptide is or includes SEQ ID NO:5.

7. The isolated polypeptide of claim 1, wherein the polypeptide is or includes SEQ ID NO:6.

8. The isolated polypeptide of claim 1, further comprising four lysine residues at the polypeptide C-terminus.

9. A pharmaceutical composition comprising the isolated polypeptide of claim 1 and a pharmaceutically acceptable carrier.

10. A method of inhibiting replication of a SARS-CoV-2 viral particle, comprising contacting the viral particle with a composition comprising the isolated polypeptide of claim 1.

11. A method of treating SARS-CoV-2 infection in a subject in need thereof, comprising administering to the subject a therapeutically effective amount of a composition comprising the isolated polypeptide of claim 1.

* * * * *

SEQUENCE LISTING

```
<160> NUMBER OF SEQ ID NOS: 16

<210> SEQ ID NO 1
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: X
<222> LOCATION: (1)..(1)
<223> OTHER INFORMATION: Naphthyl group
<220> FEATURE:
<221> NAME/KEY: X
<222> LOCATION: (6)..(6)
<223> OTHER INFORMATION: alpha-aminoisobutyric acid
<220> FEATURE:
<221> NAME/KEY: X
<222> LOCATION: (10)..(10)
<223> OTHER INFORMATION: alpha-aminoisobutyric acid

<400> SEQUENCE: 1

Xaa Phe Phe Thr Leu Xaa Phe Leu Thr Xaa Thr Glu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group

<400> SEQUENCE: 2

Xaa Phe Phe Ser Leu Ala Phe Leu Thr Ala Thr Glu
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group
<220> FEATURE:
<221> NAME/KEY: X
```

```
<222> LOCATION: (6)..(6)
<223> OTHER INFORMATION: alpha-aminoisobutyric acid
<220> FEATURE:
<221> NAME/KEY: X
<222> LOCATION: (10)..(10)
<223> OTHER INFORMATION: alpha-aminoisobutyric acid

<400> SEQUENCE: 3

Xaa Phe Phe Ser Leu Xaa Phe Leu Ser Xaa Thr Glu
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group

<400> SEQUENCE: 4

Xaa Phe Phe Thr Leu Ala Phe Leu Thr Ala Thr Glu
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group
<220> FEATURE:
<221> NAME/KEY: X
<222> LOCATION: (6)..(6)
<223> OTHER INFORMATION: Alpha-aminoisobutyric acid
<220> FEATURE:
<221> NAME/KEY: X
<222> LOCATION: (10)..(10)
<223> OTHER INFORMATION: Alpha-aminoisobutyric acid

<400> SEQUENCE: 5

Xaa Phe Phe Ser Leu Xaa Phe Leu Ser Xaa Ser Glu
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group
<220> FEATURE:
<221> NAME/KEY: X
<222> LOCATION: (6)..(6)
<223> OTHER INFORMATION: Alpha-aminoisobutyric acid
<220> FEATURE:
<221> NAME/KEY: X
<222> LOCATION: (10)..(10)
<223> OTHER INFORMATION: Alpha-aminoisobutyric acid

<400> SEQUENCE: 6

Xaa Phe Phe Met Leu Xaa Phe Leu Met Xaa Met Glu
1               5                   10
```

-continued

```
<210> SEQ ID NO 7
<211> LENGTH: 32
<212> TYPE: PRT
<213> ORGANISM: SARS-CoV-2

<400> SEQUENCE: 7

Glu Glu Thr Gly Thr Leu Ile Val Asn Ser Val Leu Leu Phe Leu Ala
1               5                   10                  15

Phe Val Val Phe Leu Leu Val Thr Leu Ala Ile Leu Thr Ala Leu Arg
            20                  25                  30

<210> SEQ ID NO 8
<211> LENGTH: 32
<212> TYPE: PRT
<213> ORGANISM: SARS-CoV

<400> SEQUENCE: 8

Glu Glu Thr Gly Thr Leu Ile Val Asn Ser Val Leu Leu Phe Leu Ala
1               5                   10                  15

Phe Val Val Phe Leu Leu Val Thr Leu Ala Ile Leu Thr Ala Leu Arg
            20                  25                  30

<210> SEQ ID NO 9
<211> LENGTH: 32
<212> TYPE: PRT
<213> ORGANISM: MERS-CoV

<400> SEQUENCE: 9

Glu Arg Ile Gly Leu Phe Ile Val Asn Phe Phe Ile Phe Thr Val Val
1               5                   10                  15

Cys Ala Ile Thr Leu Leu Val Cys Met Ala Phe Leu Thr Ala Thr Arg
            20                  25                  30

<210> SEQ ID NO 10
<211> LENGTH: 32
<212> TYPE: PRT
<213> ORGANISM: HCoV-HKU1

<400> SEQUENCE: 10

Asn Asp Thr Ala Trp Tyr Ile Gly Gln Ile Leu Val Leu Val Leu Phe
1               5                   10                  15

Cys Leu Ile Ser Leu Ile Phe Val Val Ala Phe Leu Ala Thr Ile Lys
            20                  25                  30

<210> SEQ ID NO 11
<211> LENGTH: 32
<212> TYPE: PRT
<213> ORGANISM: HCoV-OC43

<400> SEQUENCE: 11

Ala Asp Thr Val Trp Tyr Val Gly Gln Ile Ile Phe Ile Val Ala Ile
1               5                   10                  15

Cys Leu Leu Val Thr Ile Val Val Ala Phe Leu Ala Thr Phe Lys
            20                  25                  30

<210> SEQ ID NO 12
<211> LENGTH: 31
<212> TYPE: PRT
<213> ORGANISM: HCoV-NL63
```

```
<400> SEQUENCE: 12

Asp Asp Asn Gly Ile Val Leu Asn Ser Ile Leu Trp Leu Leu Val Met
1               5                   10                  15

Ile Phe Phe Phe Val Leu Ala Met Thr Phe Ile Lys Leu Ile Gln
            20                  25                  30

<210> SEQ ID NO 13
<211> LENGTH: 31
<212> TYPE: PRT
<213> ORGANISM: HCoV-229E

<400> SEQUENCE: 13

Asp Asp His Ala Leu Val Val Asn Val Leu Leu Trp Cys Val Val Leu
1               5                   10                  15

Ile Val Ile Leu Leu Val Cys Ile Thr Ile Ile Lys Leu Ile Lys
            20                  25                  30

<210> SEQ ID NO 14
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group
<220> FEATURE:
<221> NAME/KEY: X
<222> LOCATION: (6)..(6)
<223> OTHER INFORMATION: alpha-aminoisobutyric acid
<220> FEATURE:
<221> NAME/KEY: X
<222> LOCATION: (10)..(10)
<223> OTHER INFORMATION: alpha-aminoisobutyric acid

<400> SEQUENCE: 14

Xaa Phe Phe Thr Leu Xaa Phe Leu Thr Xaa Thr Glu Lys Lys Lys Lys
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: Synthetic peptide
<220> FEATURE:
<221> NAME/KEY: X
<222> LOCATION: (1)..(1)
<223> OTHER INFORMATION: Naphthyl group
<220> FEATURE:
<221> NAME/KEY: X
<222> LOCATION: (6)..(6)
<223> OTHER INFORMATION: Alpha-aminoisobutyric acid
<220> FEATURE:
<221> NAME/KEY: X
<222> LOCATION: (10)..(10)
<223> OTHER INFORMATION: Alpha-aminoisobutyric acid

<400> SEQUENCE: 15

Xaa Phe Phe Met Leu Xaa Phe Leu Met Xaa Met Glu Lys Lys Lys Lys
1               5                   10                  15

<210> SEQ ID NO 16
<211> LENGTH: 12
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: X
<222> LOCATION: (1)..(1)
<223> OTHER INFORMATION: Naphthyl group
<220> FEATURE:
<221> NAME/KEY: X
<222> LOCATION: (4)..(4)
<223> OTHER INFORMATION: T, S, or M
<220> FEATURE:
<221> NAME/KEY: X
<222> LOCATION: (6)..(6)
<223> OTHER INFORMATION: Alpha-aminoisobutyric acid or A
<220> FEATURE:
<221> NAME/KEY: X
<222> LOCATION: (9)..(9)
<223> OTHER INFORMATION: T, S, or M
<220> FEATURE:
<221> NAME/KEY: X
<222> LOCATION: (10)..(10)
<223> OTHER INFORMATION: Alpha-aminoisobutyric acid or A
<220> FEATURE:
<221> NAME/KEY: X
<222> LOCATION: (11)..(11)
<223> OTHER INFORMATION: T, S, or M

<400> SEQUENCE: 16

Xaa Phe Phe Xaa Leu Xaa Phe Leu Xaa Xaa Xaa Glu
1               5                   10
```